United States Patent [19]

Mizutani et al.

[11] Patent Number: 4,915,727

[45] Date of Patent: * Apr. 10, 1990

[54] PLANT MALE STERILANT

[75] Inventors: Masato Mizutani, Toyonaka; Masao Shiroshita, Nishinomiya; Nobuaki Mito, Takarazuka; Hiroki Okuda; Masaharu Sakaki, both of Toyonaka, all of Japan

[73] Assignee: Sumitomo Chemical Company, Limited, Osaka, Japan

[ * ] Notice: The portion of the term of this patent subsequent to Oct. 24, 2006 has been disclaimed.

[21] Appl. No.: 137,703

[22] Filed: Dec. 24, 1987

[30] Foreign Application Priority Data

Dec. 26, 1986 [JP] Japan ............................... 61-314254
Dec. 26, 1986 [JP] Japan ............................... 61-314255

[51] Int. Cl.$^4$ .............................................. A01N 43/58
[52] U.S. Cl. ........................................ 71/92; 544/235; 560/34; 562/439; 564/167
[58] Field of Search ............................................ 71/92

[56] References Cited

U.S. PATENT DOCUMENTS 4,729,782 3/1988 Labovitz et al. ...................... 71/92

FOREIGN PATENT DOCUMENTS 138661 4/1985 European Pat. Off. .
0197226 10/1986 European Pat. Off. .

OTHER PUBLICATIONS

Sandison et al., J. Chem. Soc. Chem. Comm., 1974, 752.
Ames et al., Synthesis, 1983, 52.
Prudchenko et al., Chemical Abstracts, vol. 69, No. 26059q, (1986).

Primary Examiner—Mukund J. Shah
Assistant Examiner—E. Bernhardt
Attorney, Agent, or Firm—Armstrong, Nikaido, Marmelstein, Kubovcik & Murray

[57] ABSTRACT

A plant male sterilant, which comprises as an active ingredient a compound having the formula (I):

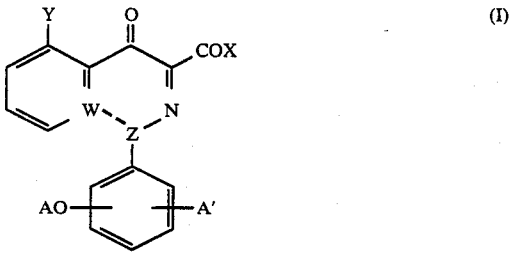

in which X is —OH, —O$^-$M$^+$, —OR$^1$ or

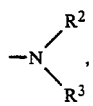

wherein M$^+$ is an alkali metal cation, an alkaline earth metal cation or

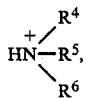

in which
R$^4$, R$^5$ and R$^6$ are the same or different and each is hydrogen, C$_1$–C$_6$ alkyl, C$_3$–C$_4$ alkenyl group, C$_3$–C$_4$ alkynyl, C$_3$–C$_8$ cycloslkyl, benzyl or phenyl group;
R$^1$ is a C$_1$–C$_9$ alkyl, a C$_3$–C$_6$ alkenyl, a C$_3$–C$_4$ alkynyl, C$_1$–C$_3$ alkoxy (C$_1$–C$_4$)-alkyl, C$_3$–C$_8$ cycloalkyl, benzyl or phenyl; and
R$^2$ and R$^3$ are the same or different and each is hydrogen, C$_1$–C$_6$ alkyl, C$_3$–C$_4$ alkenyl, C$_3$–C$_4$ alkynyl, C$_3$–C$_8$ cycloalkyl, a benzyl group in which at most two hydrogen atoms at the α-position thereof may be substituted by methyl, C$_2$–C$_3$ hydroxyalkyl or a phenyl in which at most three hydrogen atoms thereof may be substituted by the same or different C$_1$–C$_2$ alkyl;
Y is fluorine, chlorine, trifluoromethyl or C$_1$–C$_6$ alkoxy;
A is CF$_3$, CHF$_2$, CF$_2$Cl, CF$_2$Br, CF$_2$CHF$_2$, CH$_2$CF$_3$, CF$_2$CHCl$_2$, CFClCHFCl, CF$_2$CHFCl or CF$_2$CHFCF$_3$;
A' is hydrogen or halogen; and
W and Z are C-F and N-H respectively with non-bonding or are taken together to form C-N, provided that X is OR$^1$ in case that W and Z are C-F and N-H respectively.

The combination of the present invention can easily and efficiently induce male sterility in a plant without losing a pollination ability of the plant.

7 Claims, No Drawings

PLANT MALE STERILANT

BACKGROUND OF THE INVENTION

The present invention realtes to a composition for inducing male sterility in a plant which comprises a compound, as an active ingredient, having the formula (I):

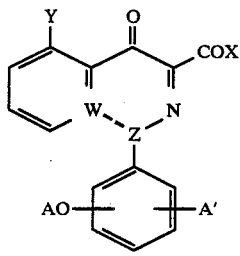

in whcih X is —OH, —O$^-$M$^+$—OR$^1$ or

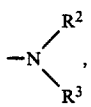

wherein M$^+$is an alkali metal cation, an alkaline earth metal cation or

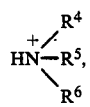

in which
- R$^4$, R$^5$ and R$^6$ are the same or different and each is hydrogen, a C$_1$–C$_6$ alkyl, a C$_3$–C$_4$ alkenyl, a C$_3$–C$_4$ alkynyl, a C$_3$–C$_8$ cycloalkyl, benzyl or phenyl;
- R$^1$ is a C$_1$–C$_9$ alkyl, a C$_3$–C$_6$ alkenyl, a C$_3$–C$_4$ alkynyl, a C$_1$–C$_3$ alkoxy (C$_1$–C$_4$) alkyl, a C$_3$–C$_8$ cycloalkyl, benzyl or phenyl; and
- R$^2$ and R$^3$ are the same or different and each is hydrogen, a C$_1$–C$_6$ alkyl, a C$_3$–C$_4$ alkenyl, a C$_3$–C$_4$ alkynyl, a C$_3$–C$_8$ cycloalkyl, a benzyl in which at most two of hydrogen atoms at the α-position thereof may be sustituted by methyl, a C$_2$–C$_3$ hydroxyalkyl or a phenyl in which at most three of hydrogen atoms thereof may be substituded by the same or different C$_1$–C$_2$ alkyl;
- Y is fluorine, chlorine, a trifluoromethyl or a C$_1$–C$_6$ alkoxy;
- A is CF$_3$, CHF$_2$, CF$_2$Cl, CF$_2$BR, CF$_2$CHF$_2$, CH$_2$CF$_3$, CF$_2$CHCl$_2$, CFClCHFCl, CF$_2$CHFCl or CF$_2$CHFCF$_3$;
- A' is hydrogen or halogen; and
- W and Z are C-F and N-H respectively with nonbonding, or are taken together to form C-N, provided that X is OR$^1$ in case that W and Z are C-F and N-H respectively, and an agriculturally accetpable carrier or diluent.

In recent years, the food crisis has caused public discussion and the increase of producing food has become a big problem. Under this situation, the production of hydrid seeds has attracted attention.

It is known that the first filial generation plant has many outstanding characters such as an increased yield compared with its parent variety, owing to its vigorous growth. In order to obtain hydrid seeds it is necessary to prevent a self-pollination of a female parent and stamens of the female parent have to be removed for that purpose.

Hitherto, there have made a lot of efforts for the operation of removing stamens, i.e. castration, and also, since grains having a high rate of self-pollination, e.g. rice, wheat, and the like, have both stamens and pistils in small spikelet, it has been almost impossible to produce the hybrid seeds manually. There are other methods such as use of a cytoplasmic male sterility, but this method has problems such as it takes a long time for its breeding. Therefore, in recent years, it has been desired simple and sure methods to induce male sterility in plant without losing a pollination ability of the female parent.

Some kinds of cinnoline derivatives are described in some literatures [Zh. Obshch. Khim., 37, 2487 (1967): J. Chem. Soc. Chem. Commun., 1974, 752; and Synthesis, 1983, 52]and also disclosed in EP-A No. 138661 as a chemical hydridizing agent.

However, the above mentioned compounds are not necessariluy satisfied since its efficiency is insufficient or they show a chemical injury on crop.

As the result of the continuous effort of the present inventors, now it has been found that a compound having the formula (I) can induce the male sterility in plant very simply and efficiently by treating plant with the compound. Consequently the present invention is accomplished.

SUMMARY OF THE INVENTION

According to the present invention, there are provided a plant male sterilant, which comprises as an active ingredient an effective amount of a compound having the formula (I):

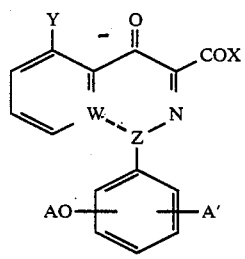

in which X is —OH, —O$^-$M$^+$, —OR$^1$ or

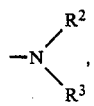

wherein M$^+$is an alkali metal cation, an alkaline earth metal cation or

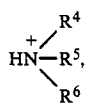

in which
- R$^4$, R$^5$ and R$^6$ are the same or different and each is hydrogen, a C$_1$–C$_6$ alkyl, a C$_3$–C$_4$ alkenyl, a C$_3$–C$_4$ alkynyl, a C$_3$–C$_8$ cycloalkyl, benzyl or phenyl;

$R^1$ is a $C_1$–$C_9$ alkyl, a $C_3$–$C_6$ alkenyl, a $C_3$–$C_4$ alkynyl, a $C_1$–$C_3$ alkoxy ($C_1$–$C_4$) alkyl, a $C_3$–$C_8$ cycloalkyl, benzyl; and $R^2$ and $R^3$ are the same or different and each is hydrogen, a $C_1$–$C_6$ alkyl, a $C_3$–$C_4$ alkenyl, a $C_3$–$C_4$ alkynyl, a $C_3$–$C_8$ cycloalkyl, a benzyl in which at most two of hydrogen atoms at the α-position thereof may be substituted by methyl, a $C_2$–$C_3$ hydroxyalkyl or a phenyl in which at most three of hydrogen atoms thereof may be substituted by the same or different $C_1$–$C_2$ alkyl;

Y is fluorine, chlorine, a trifluoromethyl or a $C_1$–$C_6$ alkoxy;

A is a $CF_3$, $CHF_2$, $CF_2CL$, $CF_2Br$, $CF_2CHF_2$, $CH_2CF_3$, $CF_2CHCl_2$, $CFClCHFCl$, $CF_2CHFCl$ or $CF_2CHFCF_3$;

A' is hydrogen or a halogen; and

W and Z are C-F and N-H respectively with non-bonding, or are taken together to form C-N, provided that X is $OR^1$ in case that W and Z are C-F and N-H respectively, and an agriculturally acceptable carrier or diluent;

a method for inducing male sterility in plant, which comprises applying an effective amount of a compound having the formula (I):

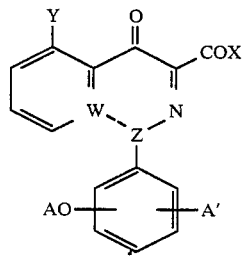

(I)

in which X is —OH, —O⁻M⁺, —OR¹ or

wherein M⁺ is an alkali metal cation, an alkaline earth metal cation or

in which $R^4$, $R^5$ and $R^6$ are the same or different and each is hydrogen, a $C_1$–$C_6$ alkyl, a $C_3$–$C_4$ alkenyl, a $C_3$–$C_4$ alkynyl, a $C_3$–$C_8$ cycloalkyl, benzyl or phenyl;

$R^1$ is a $C_1$–$C_9$ alkyl, a $C_3$–$C_6$ alkenyl, a $C_3$–$C_4$ alkynyl, a $C_1$–$C_3$ alkoxy ($C_1$–$C_4$) alkyl group, a $C_3$–$C_8$ cycloalkyl, benzyl or phenyl; and $R^2$ and $R^3$ are the same or different and each is hydrogen, a $C_1$–$C_6$ alkyl, a $C_3$–$C_4$ alkenyl, a $C_3$–$C_4$ alkynyl, a $C_3$–$C_8$ cycloalkyl, a benzyl in which at most two of hydrogen atoms at the α-position thereof may be susbstitued by methyl, a $C_2$–$C_3$ hydroxyalkyl or a phenyl in which at most three of hydrogren atoms thereof may be substituded by the same or different $C_1$–$C_2$ alkyl;

Y is fluorine, chlorine, a trifluoromethyl or a $C_1$–$C_6$ alkoxy;

A is a $CF_3$, $CHF_2$, $CF_2Cl$, $CF_2Br$, $CF_2CHF_2$, $CH_2CF_3$, $CF_2CHCl_2$, $CFClCHFCl$, $CF_2CHFCl$ or $CF_2CHFCF_3$;

A' is hydrogen or a halogen; and

W and Z are C-F and N-H respectively with non-bonding, or are taken together to form C-N, provided that X is $OR^1$ in case that W and Z are C-F and N-H respectively, and an agriculturally acceptable carrier or diluent to the plant;

a hydrazone derivative having the formula (II):

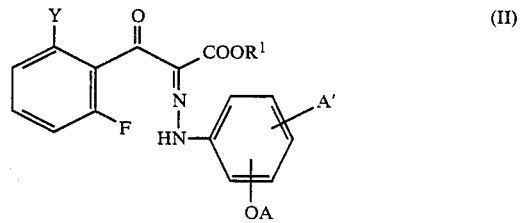

(II)

in which $R^1$ is a $C_1$–$C_9$ alkyl, a $C_3$–$C_6$ alkenyl, a $C_3$–$C_4$ alkynyl, a $C_1$–$C_3$ alkoxy ($C_1$–$C_4$) alkyl, a $C_3$–$C_8$ cycloalkyl, benzyl or phenyl group;

Y is fluorine, chlorine, a trifluoromethyl or a $C_1$–$C_6$ alkoxy;

A is $CF_3$, $CHF_2$, $CF_2Cl$, $CF_2Br$, $CF_2CHF_2$, $CH_2CF_3$, $CF_2CHCl_2$, $CFClCHFCl$, $CF_2CHFCl$ or $CF_2CHFCF_3$; and A' is hydrogen or a halogen.

DETAILED DESCRIPTION

Hereinafter, the present invention is explained in detail.

Among the compositions for inducing sterility in a plant of the present invnetion, those wherein W and Z are taken together to form C-N are preferred in efficiency. More preferred are those wherein W and Z are taken together to form C-N and X is —OH, —O⁻M⁺ or —OR¹.

Further, particularly more preferred are those wherein W and Z are taken together to form C-N, X is —OH, —O⁻M⁺ or —OR¹ and A is a dihalomethyl group or a trihalomethyl group, and among them, the most preferred are those wherein Y is fluorine atom, a trihalomethyl group or a $C_1$–$C_4$ alkoxy group.

The compositions for inducing sterility in a plant of the present invention are used for various cultivated plants, for instance, grains such as rice, wheat, barley, wild oats, rye and corn, leguminous crops such as soybean, vegetables such as eggplant, tomato and cabbage or flower and ornamental plants such as morningglory, petunia and zinnia. The compositions for inducing sterility in a plant can sufficiently induce male sterility in plant without causing any serious phytotoxicity on the plant.

That is to say, when the compositions for inducing sterility in a plant of the present invention is used, it can induce almost completely male sterility in plant without causing any undesirable side-effects on plant.

Further, as mentioned in the following Test Examples, since the sterilant of the present invention has no harmful influence on a pistil, the hybrid seeds can be easily obtained by means of cross-pollination.

Processes for preparing the compounds used as an active indgredient in sterilant of the present invention are explained as follows. Among the compounds, a compound in which W and Z are C-F and N-H respectively with non-bonding, i.e. a hydrazone derivative having the formula (II):

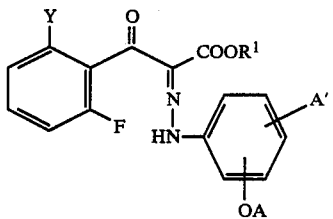
(II)

wherein $R^1$, Y, A and A' are as defined above, are obtainable by reacting a benzoylacetate derivative having the formula (III):

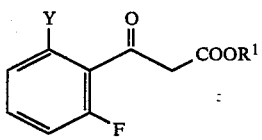
(III)

wherein $R^1$ and Y are as defined above, with the diazonium salt derivative having the formula (IV):

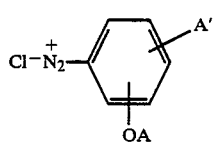
(IV)

wherein A and A' are as defined above.

The reaction is usually carried out in a solvent at a temperature of 0° to 50° C. for a period of 10 minutes to 10 hours. The compound (IV) may be used in an amount of about 1 to about 1.5 equivalents to one equivalent of the compound (III).

Examples of the solvent are, for instance, ethers (e.g. diethyl ether, diisopropyl ether, dioxane, tetrahydrofuran and diethylene glycol dimethyl ether), alcohols (e.g. methanol, ethanool, isopropanol, t-butanol, octanol, cyclohexanol, methyl cellosolve. diethylene glycol and glycerin), tertiaryamines (e.g. pyridine, triethylamine, N,N-diethylaniline, tributylamine and N-methylmorpjoline), acid amides (e.g. formamide, N,N-dimethylformamide, acetamide), water, and the like. Their mixtures are also usable.

Inorganic bases such as sodium carbonate, potassium carbonate, sodium acetate and potassium acetate may be added to the reaction mixture in order that the reaction proceeds smoothly.

After completion of the reaction, the reaction mixture is subjected to ordinary post-treatment such as extraction with an organic solvent and concentration. If desired, any conventional purification procedures such as chromatography and recrystallization may be adopted.

Among the compounds (II), which are obtainable according to the above process, those wherein A is a dihalomethyl group or a trihalomethyl group and Y is fluorine atom, a trihalomethyl group or a $C_1$–$C_4$ alkoxy groups are preferred.

The compound (IV) is obtainable according to the ordinary methods described in, for instance, Organic Functional Group Preparations, S.R. Sandler and W. Karo, Academic Press, Chapter 15(1968).

The compounds, in which W and Z are taken together to form C-N, can be prepared as follows:

(1) A cinnoline-3-carboxylate ester derivative in which X on the formula (I) is —$OR^1$, i.e. having the formula (I-1):

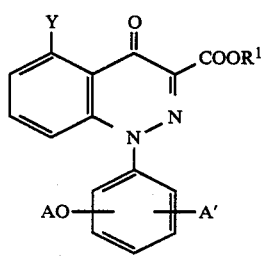
(I-1)

wherein $R^1$, Y, A and A' are as defined above, is obtainable by reacting a hydrazone derivative having the formula (V):

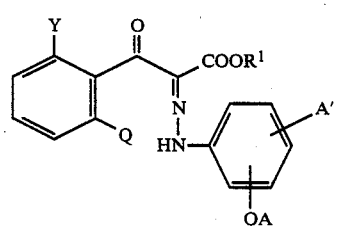
(V)

wherein $R^1$, Y, A and A' are as defined and Q is a halogen atom and when Y is fluorine atom, Q is also fluorine atom, with a dehydrohalogenating agent.

The reaction is carried out by using the dehydrohalogenating agent, in a solvent or without any solvent, at a temperature of 0° to 150° C. for a period of 10 minutes to 20 hours. The dehydrohalogenating agent may be used in an amount of about 1 to about 10 equivalents to one equivalent of the compound (V).

In order to carry out the reaction more efficiently, quaternary ammonium salts or crown ethers may be added to the reaction mixture.

Examples of the solvent are, for instance, aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate, diethyl carbonate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorphorine), acid amides (e.g. formamide, N,N-dimethylformamide, acetamide), sulfur compounds (e.g. dimethyl sufoxide, sulfolane), water, and the like. Their mixtures are also usuable.

Examples of the dehydrohalogenating agent are, for instance, organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxide (e.g. sodium methoxide, sodium ethoxide), and the like.

As for the quaternary ammonium salts, there are, for instance, benzyl triethyl ammonium chloride and tetrabutyl ammonium chloride, and the like. Examples of the crown ether are, for instance, dibenzo-18-crown-6, and the like.

After completion of the reaction, the reaction mixture is subjected to ordinary post-treatments such as collection of crystals by means of addition of water, extraction with an organic solvent and concentration. If desired, purification procedures such as chromatography and recrystallization may be adopted to obtain the compound (I-1).

(2) A cinnoline-3-carboxylic acid derivative, in which X on the formula (I) is hydroxyl group, i.e. having the formula (I-2):

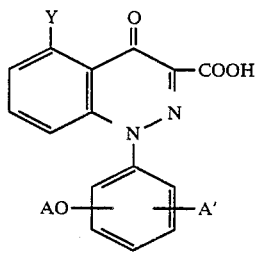

wherein Y, A and A' are as defined above, can be prepared by subjecting the compound (I-1) to hydrolysis.

The reaction is usually carried out in either water or a mixture of water and other solvents such as alcohols (e.g. methanol, ethanol, isopropanol, diethylene glycol, glycerin), ketones (e.g. acetone), ethers (e.g. tetrahydrofuran, dioxane), nitriles (e.g. acetonitrile), acid amides (e.g. formamoide, N,N-dimethylformamide) and sulfur compounds (e.g. dimethyl sulfoxide).

Usually, there is added acids or alkalis to the reaction mixture in an amount of about 1 to about 100 equivalents to one equivalent of the compound (I-1).

The reaction can be accomplished at a temperature of 20° to 100° C. for a period of 30 minutes to 10 hours. Examples of the acids are, for instance, hydrochloric acid, sulfuric acid, nitric acid, and the like. Examples of the alkalis are, for instance, sodium hydroxide, potassium hydroxide, and the like.

In case of using the alkalis, after completion of the reaction, the reaction mixture is subjected to the reaction of neutralization with acids such as hydrochloric acid, sulfuric acid, formic acid and acetic acid. As for post-treatment of the reaction mixture, if there are precipitated crystals, they are collected by filtration, otherwise the compound (I-2) is obtainable by subjecting the reaction mixture to purification procedures such as extraction with an organic solvent and concentration.

(3) A cinnoline-3-carboxylic acid derivative, in which X on the formula (I) is $-O^-M^+$, i.e. having the formula (I-3):

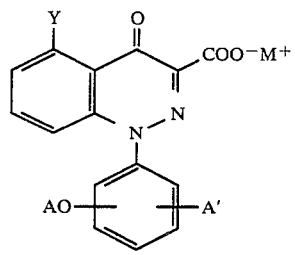

wherein Y, A and A' are as defined above and $M^+$ is an alkali metal cation or an alkaline earth metal cation, can be prepared by reacting the compound (I-2) with a metal hydroxide having the formula: $M^+OH^-$, wherein $M^+$ is as defined above.

Examples of the metal hydroxide are, for instance, lithium hydroxide, sodium hydroxide, potassium hydroxide, calcium hydroxide, and the like.

The raction is usually carried out in water and the metal hydroxide may be employed in an amount of about 0.7 to about 1 equivalent to one equivalent of the compound (I-2).

The reaction can be accomplished at a temperature of 0° to 50° C. for a period of 5 minutes to 5 hours. After completion of the reaction, if desired, a water layer is washed with an organic solvent and the compound (I-3) is obtainable by concentrating the water layer.

(4) A cinnoline-3-carboxylic acid amine salt derivative, in which X on the formula (I) is

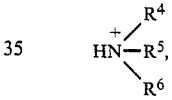

i.e. having the formula (I-4):

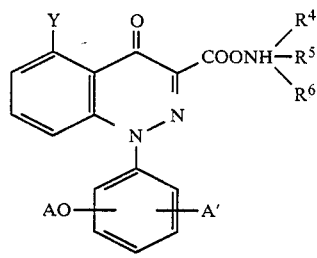

wherein $R^4$, $R^5$, $R^6$, Y, A and A' are as defined above, can be prepared by reacting the compound (I-2) with an amine having the formula (VI):

wherein $R^4$, $R^5$ and $R^6$ are as defined above.

The reaction is usually carried out in a solvent or without any solvent at a temperature of 0° to 100° C. for a period of 5 minutes to 8 hours. The amine (VI) may be used in an amount of about 1 to about 10 equivalents to one equivalent of the compound (I-2).

Examples of the solvent are, for instance, aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), alcohols (e.g. methanol, ethanol, isopropanol, t-butanol, octanol, cyclohexanol, methyl cellosolove, diethylene glycol, glycerin), esters (e.g. ethyl formate, ethyl acetate, butyl acetate, diethyl carbonate), nitro compounds (e.g. nitro ethane, nitro benzene), nitriles (e.g. acetonitrile, isobutylonitrile), water, and the like. Their mixtures are also usable.

After completion of the reaction, the reaction mixture is subjected to ordinary post-treatments such as concentration and, if necessary, to purification procedures such as recrystallization to give the compound (I-4).

(5) A cinnoline-3-carboxylic acid amide derivative, in which X on the formula (I) is

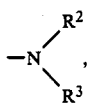

i.e. having the formula (I-5):

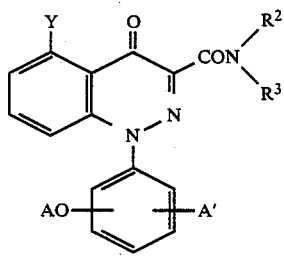

(I-5)

wherein $R^2$, $R^3$, Y, A and A' are as defined above, can be prepared by reacting a cinnoline-3-carboxylic acid halide having the formula (VII):

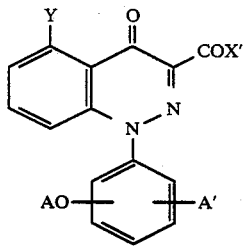

(VII)

wherein Y, A and A' are as defined above and X' is a halogen atom, with an amine having the formula (VIII):

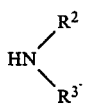

(VIII)

wherein $R^2$ and $R^3$ are as defined above.

The reaction is usually carried out in a solvent or without any solvent, in the presense of a dehydrohalogenating agent at a temperature of 0° to 50° C. for a period of 10 minutes to 3 hours. The compound (VIII) and the dehydrohalogenating agent may be used in an amount of about 1 to about 5 equivalents to and about 1 to about 2 equivalents to one equivalent of the compound (VII) respectively.

Examples of the solvent are, for instance, aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), esters (e.g. ethyl formate, ethyl acetate, butyl acetate, diethyl carbonate), nitro compounds (e.g. nitroethane, nitrobenzene), nitriles (e.g. acetonitrile, isobutylonitrile), tertiary amines (e.g. pyridine, triethylamine, N,N-diethylaniline, tributylamine, N-methylmorphorine), acid amines (e.g. formamide, N,N-dimethylformamide, acetamide), sulfur compounds (e.g. dimethyl sulfoxide, sulfolane), water, and the like. The mixtures of them are also usable.

Examples of the dehydrohalogenating agent are organic bases such as pyridine, triethylamine, N,N-diethylaniline.

After completion of the reaction, the reaction mixture is subjected to ordinary post-treatments such as extraction with an organic solvent and concentration to obtain the compound (I-5). If necessary, purification procedures such as chromatography and recrystallization may be adopted.

On the other hand, the compound (VII) can be easily obtained by subjecting the compound (I-2) to ordinary acid halogenation.

Typical examples of the compound contained in the plant male sterilant of the present invention, which can be prepared through the above procedures, are shown in Table 1 and Table 2.

TABLE 1

| OA | A' | X | Y |
|---|---|---|---|
| 4-OCF₃ | H | OH | F |
| " | " | OK | " |
| " | " | ONH₄ | " |
| " | " | OC₂H₅ | " |
| " | " | N(C₂H₅)₂ | " |
| " | " | N(CH₂CH=CH₂)₂ | " |
| " | " | OH | Cl |
| " | " | OK | " |
| " | " | OC₂H₅ | " |
| " | " | NH—⟨cyclohexyl⟩ | " |
| " | " | OC₂H₅ | CF₃ |
| " | " | ONa | OCH₃ |
| " | " | OK | OC₄H₉-n |
| 3-OCF₃ 4-OCHF₂ | " | OC₂H₅ | F |
| " | " | OH | " |
| " | " | OK | " |
| " | " | OCH₃ | " |
| " | " | OC₂H₅ | " |
| " | " | OH | Cl |
| " | " | ONa | " |
| " | " | OC₂H₅ | " |

TABLE 1-continued

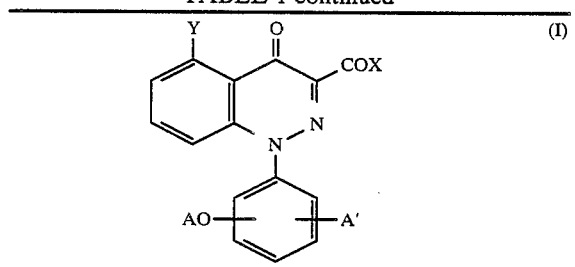

| OA | A' | X | Y |
|---|---|---|---|
| " | " | OC4H9-n | " |
| " | " | OC4H9-i | " |
| 4-OCHF2 | H | OC3H7-n | CF3 |
| " | " | OK | OC2H5 |
| " | " | OH | OCH3 |
| " | 2-F | OK | F |
| " | " | OC2H5 | Cl |
| 2-OCHF2 | 4-F | OK | CF3 |
| " | " | OCH3 | OC3H7-i |
| 3-OCHF2 | H | OC2H5 | F |
| 4-OCF2Cl | " | OK | " |
| 4-OCF2Br | " | OK | " |
| " | " | OC2H5 | Cl |
| 4-OCF2Br | " | ONa | CF3 |
| 4-OCF2CHF2 | " | OC2H5 | F |
| " | " | OH | Cl |
| " | " | OK | " |
| " | " | OC2H5 | " |
| 4-OCH2CF3 | " | " | F |
| " | " | OH | Cl |
| " | " | ONa | " |
| " | " | OC2H5 | " |
| " | " | OC4H9-n | " |
| " | " | OK | F |
| 4-OCF2CHCl2 | " | OH | " |
| 4-OCFClCHFCl | " | OC2H5 | Cl |
| 4-OCF2CHFCl | " | OK | OCH3 |
| 4-OCF2CHFCF3 | " | OC2H5 | F |

TABLE 2

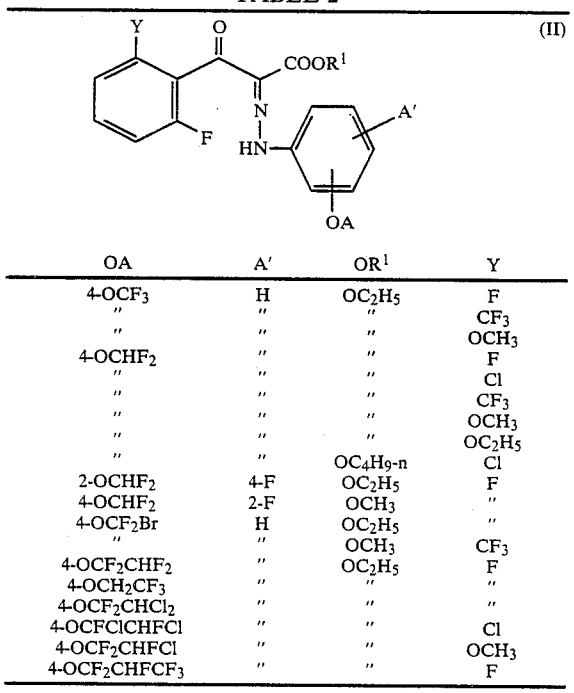

| OA | A' | OR¹ | Y |
|---|---|---|---|
| 4-OCF3 | H | OC2H5 | F |
| " | " | " | CF3 |
| " | " | " | OCH3 |
| 4-OCHF2 | " | " | F |
| " | " | " | Cl |
| " | " | " | CF3 |
| " | " | " | OCH3 |
| " | " | " | OC2H5 |
| " | " | OC4H9-n | Cl |
| 2-OCHF2 | 4-F | OC2H5 | F |
| 4-OCHF2 | 2-F | OCH3 | " |
| 4-OCF2Br | H | OC2H5 | " |
| " | " | OCH3 | CF3 |
| 4-OCF2CHF2 | " | OC2H5 | F |
| 4-OCH2CF3 | " | " | " |
| 4-OCF2CHCl2 | " | " | " |
| 4-OCFClCHFCl | " | " | Cl |
| 4-OCF2CHFCl | " | " | OCH3 |
| 4-OCF2CHFCF3 | " | " | F |

The present invention is more specifically described and explained by means of the following Examples, wherein the compound number of the active ingedient corresponds to the one in Table 3 and Table 4. It is to be understood that the present invention is not limited to the Examples and various changers and modifications can be made without departing from the scope and spirit of the present invention.

EXAMPLE 1

Preparation of the compound No. 45

To 551 mg of 4-trifluoromethoxyaniline was added 6 ml of water and 2 ml of concentrated hydrochloric acid to prepare a solution of hydrochloric acid salt. And thereto, a solution of 236 mg of sodium nitrite in 2 ml of water was added dropwise over about 5 minutes while cooling with ice to form a diazonium salt.

The obtained solution was added dropwise to a solution of 710 mg of ethyl 2,6-difluorobenzoylacetate in a mixture of 15 ml of 70% methanol and 2 ml of pyridine at 10° to 20° C. over about 10 minutes, followed by stirring the reaction mixture for 1 hour at room temperature.

After adding 30 ml of water thereto, the resultant mixture was extracted twice with 30 ml of ethyl acetate. After the extract was concentrated, the residue was purified by means of silica gel column chromatography with a mixture of n-hexane and ethyl acetate (v/v=10/1) to give 1048 mg of ethyl 2-[(4-trifluoromethoxyphenyl)-1,1-diazanediyl]-(2,6-difluorobenzoyl)acetate (yield: 80.9% by mole).

EXAMPLE 2

Preparation of the compound No. 49

To 1048 mg of 4-difluoromethoxyaniline was added 6 ml of water and 3 ml of concentrated hydrochloric acid to prepare a solution of hydrochloric acid salt. And thereto, a solution of 500 mg of sodium nitrite in 3 ml of water was added dropwise over about 5 minutes while cooling with ice to form a diazonium salt.

The obtained solution was added dropwise to a solution of 1.70 g of ethyl 2,6-difluorobenzoylacetate (purity: ca. 80%) in a mixture of 25 ml of 70% methanol and 3 ml of pyridine at 10° to 20° C. over about 10 minutes, followed by stirring the resultant solution for 1 hour at room temperature.

After adding 50 ml of water thereto, the reaction mixture was extracted twice with 40 ml of ethyl acetate. After the extract was concentrated, the residue was purified by means of silica gel column chromatography with a mixture of n-hexane and ethyl acetate (v/v=10/1) to give 1.96 g of ethyl 2-[(4-difluoromethoxyphenyl)-1,1-diazanediyl]-(2,6-difluorobenzoyl)acetate (yield: 82.7% by mole).

EXAMPLE 3

Preparation of the compound No. 3

There were added 4.24 g of ethyl 2-[(4-trifluoromethoxyphenyl)-1,1-diazanediyl]-(2,6-difluorobenzoyl)acetate, 1.41 g of potassium carbonate and 10 mg of dibenzo-18-crown-6 to 20 ml of N,N-dimethylformamide, and the resultant mixture was heated for 1 hour at 100° C.

After cooling the reaction mixture to room temperature, the mixture was poured into 100 ml of ice-water. After being allowed to stand for 2 hours, precipitated crystals were collected by filtration.

The crystals were washed twice with 20 ml of water and then dried under reduced pressure to give 3.93 g of ethyl 1-(4-trifluoromethoxyphenyl)-1,4-dihydro-4-oxo-5-fluorocinnoline-3-carboxylate (yield: 97.3% by mole, m.p.: 178.0° C.).

EXAMPLE 4

Preparation of the compound No. 24

There were added 4.30 g of ethyl 2-[(4-difluoromethoxyphenyl)-1,1-diazanediyl]-(2,6-dichlorobenzoyl)acetate and 1.50 g of potassium carbonate to 25 ml of N,N-dimethylformamide, and the reaction mixture was heated for 1 hour and a half at 100° C.

After cooling the mixture to room temperature, crystals were precipitated by pouring the mixture into 100 ml of ice-water.

The crystals were collected by filtration, washed with 20 ml of water and then recrystallized from ethanol to give 3.68 g of ethyl 1-(4-difluoromethoxyphenyl)-1,4-dihydro-4-oxo-5-chlorocinnoline-3-carboxylate (yield: 93.4% by mole, m.p.: 134.0° C.).

EXAMPLE 5

Preparation of the compound No. 1

There were added 2.31 g of ethyl 1-(4-trifluoromethoxyphenyl)-1,4-dihydro-4-oxo-5-fluorocinnoline-3-carboxylate and 0.67 g of potassium hydroxide to a mixture of 24 ml of ethanol and 6 ml of water and then the resultant mixture was stirred for 7 hours at 60° to 70° C.

After cooling the reaction mixture to room temperature, the mixture was diluted with 100 ml of water and washed with 30 ml of diethyl ether. Crystals were precipitated after neutralizing the water layer with concentrated hydrochloric acid to pH 2.

The crystals were collected by filtration, washed twice with 20 ml of water, and dried under reduced pressure to give 2.14 g of 1-(4-trifluoromethoxyphenyl)-1,4-dihydro-4-oxo-5-fluorocinnoline-3-carboxylic acid (yield: 99.5% by mole, m.p.: 200°–205° C. (dec.)).

EXAMPLE 6

Preparation of the compound No. 2

There were added 405 mg of 1-(4-trifluoromethoxyphenyl)-1,4-dihydro-4-oxo-5-fluorocinnoline-3-carboxylic acid and 1.21 ml of 0.827M aqueous solution of potassium hydroxide to 10 ml of water and then the resultant suspension was stirred for 3 hours at room temperature. The reaction mixture was washed with 10 ml of ethyl acetate.

After removing the water, the obtained crystals were dried to give 406 mg of potassium 1-(4-trifluoromethoxyphenyl)-1,4-dihydro-4-oxo-5-fluorocinnoline-3-carboxylate (yield: 100% by mole, m.p.: 198°–213° C. (dec.)).

EXAMPLE 7

Preparation of the compound No. 4

There were added 368 mg of 1-(4-trifluoromethoxyphenyl)-1,4-dihydro-4-oxo-5-fluorocinnoline-3-carboxylic acid, 179 mg of thionyl chloride and 50 mg of pyridine to 10 ml of toluene and the resultant solution was heated under reflux for 2 hours.

After cooling the reaction mixture to room temperature, the mixture was added dropwise over about 10 minutes to a solution of 146 mg of diethylamine and 152 mg of triethylamine in 10 ml of ethyl acetate while cooling with ice.

After stirring the mixture for 3 hours at room temperature, the resultant mixture was allowed to stand overnight. The mixture was poured into 30 ml of diluted hydrochloric acid with ice, and the obtained mixture was extracted twice with 20 ml of ethyl acetate.

The organic layer was washed with 10 ml of each of saturated sodium bicarbonate solution, saturated saline solution and dried over anhydrous magnesium sulfate.

After the extract was concentrated, the residue was purified by means of silica gel column chromatography with a mixture of n-hexane and acetone (v/v=3/1) to give 143 mg of N,N-diethyl-1-(4-trifluoromethoxyphenyl)-1,4-dihydro-4-oxo-5-fluorocinnoline-3-carboxamide (yield: 33.8% by mole, m.p.: 118.5° C.).

Some examples of the present invention prepared in the same manner as the above are shown in Table 3 and Table 4.

TABLE 3

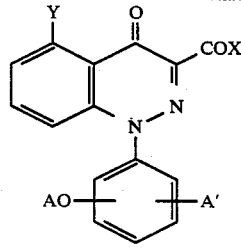

| Compound No. | OA | A' | X | Y | physical properties |
|---|---|---|---|---|---|
| 1 | 4-OCF$_3$ | H | OH | F | m.p. 200–205° C. (dec.) |
| 2 | " | " | OK | " | m.p. 198–213° C. (dec.) |
| 3 | 4-OCF$_3$ | " | OC$_2$H$_5$ | " | m.p. 178.0° C. |
| 4 | " | " | N(C$_2$H$_5$)$_2$ | " | m.p. 118.5° C. |
| 5 | " | " | 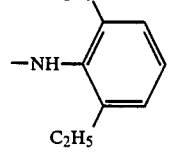 | " | m.p. 194.0° C. |

TABLE 3-continued

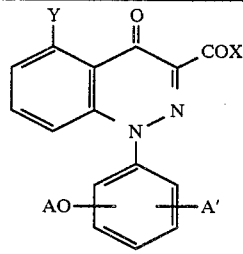

| Compound No. | OA | A' | X | Y | physical properties |
|---|---|---|---|---|---|
| 6 | " | " | OH | Cl | m.p. 210.0° C. |
| 7 | " | " | OK | " | m.p. 262.0° C. |
| 8 | " | " | OC$_2$H$_5$ | " | m.p. 114.6° C. |
| 9 | " | " | OH | CF$_3$ | m.p. 238–240° C. |
| 10 | " | " | ONa | " | m.p. 182–187° C. |
| 11 | " | " | OC$_2$H$_5$ | " | m.p. 133.0° C. |
| 12 | " | " | OH | OCH$_3$ | m.p. 265–269° C. |
| 13 | " | " | ONa | " | m.p. 215–220° C. |
| 14 | " | " | OC$_2$H$_5$ | " | m.p. 154.2° C. |
| 15 | " | " | " | OC$_2$H$_5$ | m.p. 142.4° C. |
| 16 | 3-OCF$_3$ | " | OH | F | m.p. 233.8° C. |
| 17 | " | " | ONa | " | m.p. 170–175° C. |
| 18 | " | " | OC$_2$H$_5$ | " | m.p. 130.0° C. |
| 19 | 4-OCHF$_2$ | H | OH | F | m.p. 270–276° C. |
| 20 | " | " | OK | " | m.p. 198–210° C. (dec.) |
| 21 | " | " | OC$_2$H$_5$ | " | m.p. 137.6° C. |
| 22 | " | " | OH | Cl | m.p. 228.0° C. |
| 23 | " | " | ONa | " | m.p. 199.0° C. |
| 24 | " | " | OC$_2$H$_5$ | " | m.p. 134.0° C. |
| 25 | " | " | OC$_4$H$_9$-n | " | $n_D^{22.5}$ 1.5890 |
| 26 | " | " | OC$_4$H$_9$-i | " | m.p. 111.0° C. |
| 27 | " | " | OH | CF$_3$ | m.p. 244.7° C |
| 28 | " | " | ONa | " | m.p. 182–195° C. |
| 29 | " | " | OC$_2$H$_5$ | " | m.p. 133–136° C. |
| 30 | " | " | " | OCH$_3$ | m.p. 135.4° C. |
| 31 | " | " | " | OC$_2$H$_5$ | m.p. 174.6° C. |
| 32 | " | 4-F | OH | F | m.p. 229.9° C. |
| 33 | " | " | ONa | " | m.p. 195–198° C. |
| 34 | " | " | OC$_2$H$_5$ | " | m.p. 161.6° C. |
| 35 | " | " | OH | Cl | m.p. 221.2° C. |
| 36 | " | " | ONa | " | m.p. 210–215° C. |
| 37 | " | " | OC$_2$H$_5$ | " | m.p. 226.4° C. |
| 38 | 4-OCF$_2$CHF$_2$ | H | " | F | m.p. 180.9° C. |
| 39 | " | " | " | Cl | m.p. 133.0° C. |
| 40 | 4-OCH$_2$CF$_3$ | " | " | F | m.p. 115.6° C. |
| 41 | " | " | OH | Cl | m.p. 276.0° C. |
| 42 | " | " | ONa | " | m.p. 201.0° C. |
| 43 | " | " | OC$_2$H$_5$ | " | m.p. 142.0° C. |
| 44 | " | " | OC$_4$H$_9$-n | " | $n_D^{22.5}$ 1.5785 |

TABLE 4

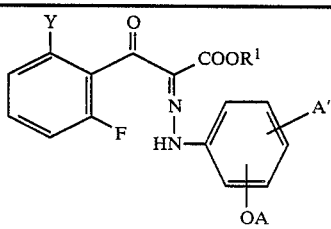 (II)

| Compound No. | OA | A' | OR$^1$ | Y | physical properties |
|---|---|---|---|---|---|
| 45 | 4-OCF$_3$ | H | OC$_2$H$_5$ | F | m.p. 77.3° C. |
| 46 | " | " | " | OCH$_3$ | m.p. 177.5° C. |
| 47 | " | " | " | OC$_2$H$_5$ | $n_D^{22.0}$ 1.5140 |
| 48 | 3-OCF$_3$ | " | " | F | m.p. 64.5° C. |
| 49 | 4-OCHF$_2$ | " | " | " | m.p. 87.6° C. |
| 50 | " | " | " | CF$_3$ | m.p. 73.5° C. |
| 51 | 4-OCHF$_2$ | H | " | OC$_2$H$_5$ | $n_D^{22.0}$ 1.5120 |
| 52 | 2-OCHF$_2$ | 4-F | " | F | m.p. 126.7° C. |
| 53 | " | " | " | Cl | $n_D^{22.0}$ 1.5070 |

TABLE 4-continued

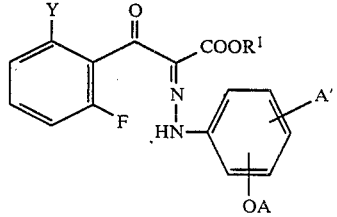 (II)

| Compound No. | OA | A' | OR$^1$ | Y | physical properties |
|---|---|---|---|---|---|
| 54 | 4-OCF$_2$CHF$_2$ | H | " | F | m.p. 78.6° C. |
| 55 | 4-OCH$_2$CF$_3$ | " | " | " | m.p. 100.5° C. |
| 56 | " | " | " | Cl | m.p. 123.0° C. |

Hereinafter, the method of the present invention for inducing male sterility in a plant is explained.

On the practical usage of the compounds as described above as an active ingredient of compositions for inducing sterility in a plant of the present invention, they can be applied in conventional preparation forms such as an emulsifiable concentrate, a wettable powder, a flowable, powder a granule and a liquid formulation in combination with a conventional solid carrier, liquid carrier, surface active agent or an auxiliary substance for formulation.

The content of the compounds of the present invention as the active ingredient in such preparations is within a range of 1 to 80% by weight, preferably 2 to 70% by weight.

Examples of the solid carrier, for instanace, are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc.

As the liquid carrier, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton seed oil), dimethylsulfoxide, N,N-dimethylformamide, acetonitrile, water, etc.

Examples of the surface active agent used for emulsification, dispersion or spreading are, for instance, anionic type agents (e.g. alkylsulfates, alkylsulfonates, alkylarylsulfonates, dialkylsulfosuccinates, polyoxyethylenealkylphosphates), non-ionic type agents (e.g. polyoxyethylene alkyl ethers, polyoxyethylene alkylaryl ethers, polyoxyethylene polyoxypropylene block copolymer, sorbitan fatty acid esters, polyoxyethylene sorbitan fatty acid esters), etc.

Examples of the auxiliary substance for formulation include ligninsulfonates, sodium alginate, polyvinyl alcohol, gum arabic, CMC (carboxymethyl cellulose), PAP (isopropyl acid phosphate), etc.

The compounds according to the present invention are usually formulated and applied to plant by foliar treatment, soil treatment or application on the surface of the water during the period of just before the reproductive growth to the flowering.

As for the application on the surface of the water, it is necessary to partition a male plant and a female plant, which are planted adjoining each other, so that the male sterilant is not absorbed by the male plant.

As for the foliar treatment and soil treatment, it is also necessary to keep the male sterilant off the male plant.

In case of using the compounds as an active ingredient of the compositions for inducing sterility in a plant, the dosage rate thereof varies depending on weather conditions, formulation used, application timing, application method, soil involved, species or varieties of the plants treated, etc. Generally, however, the dosage rate is from 5 to 10,000 grams, preferably from 20 to 3,000 grams, of the active ingredient per ha.

The plant male sterilant of the present invention formulated in the form of an emulsifiable concentrate, a wettable powder, a flowable or a liquid formulation is ordinarily employed by diluting it with water at a volume of 1 to 10 liters per are, if necessary, with addition of auxiliary substances such as a spreading agent.

On the other hand, the plant male sterilant formulated in the form of granules may be normally applied without dilution.

Examples of the spreading agent include, in addition to the surface active agents as noted above, polyoxyethylene resin acid (ester), ligninsulfonate, abietic acid salt, dinaphthylmethanedisulfonate, paraffin, etc.

Further, the compounds of the present invention may be applied in combination with plant growth regulators, herbicides, insecticides, acaricides, nematocides, fungicides, fertilizers, soil improvers, etc.

Furthermore, the sterilant of the present invention can be applied several times to the same plant by changing the application timing.

In order to obtain a lot of hybrid seeds, it is applicable to employ a method as follows:

Two parent plants are planted alternately. A number of ridges or a width thereof of each parent plant varies depending on species or varieties of the plant treated, environmental conditions, etc. After applying the sterilant of the present invention to female plant, the female plant, which is already male sterilized, are pollinated with pollens of male plant carried by wind, insects, etc, and thereby the hybrid seeds can be obtained.

Practical embodiments of preparation of the composition for inducing sterility in a plant of the present invention are illustratively shown in the following Formulation Examples wherein all parts are by weight. The compound number of the active ingredient corresponds to the one in Table 3 and Table 4.

FORMULATION EXAMPLE 1

Fifty parts of the compound No. 21, 8 parts of calcium ligninsulfonate, 2 parts of sodium laurylsulfate and 45 parts of synthetic hydrous silicate are well mixed while being powdered to obtain a wettable powder.

FORMULATION EXAMPLE 2

Ten parts of the compound No. 3, 8, 11, 14, 21, 24, 25, 26, 29, 30 or 31, 14 parts of polyoxyethylenestyrylphenyl ether, 6 parts of calcium dodecylbenzenesulfonate and 70 parts of xylene are well mixed to obtain an emulsifiable concentrate.

FORMULATION EXAMPLE 3

Two parts of the compound No. 8, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of the compound No. 1, 6, 9, 12, 19 or 45 is mixed with 3 parts of polyoxyethylene sorbitan monooleate, 3 parts of carboxymethyl cellulose and 69 parts of water and pulverized until the particle size of the mixture becomes less than 5 microns to obtain a flowable mixture.

FORMULATION EXAMPLE 5

Three parts of the compound No. 2, 7, 10, 13, 20, 23, 28 or 33, 1 part of polyoxyethylenestyrylphenyl ether and 96 parts of water are well mixed to obtain a liquid formulation.

The biological data of the compounds as the active ingredient in the plant male sterilant of the present invention are shown in the following Test Examples, wherein the compound number of the active ingredient corresponds to the one in Table 3 and Table 4.

TEST EXAMPLE 1

Sterility of wheat

Plastic pots (volume: 200 ml) were filled with artificial soil mix and seeds of wheat (variety: NORIN No. 61) were sowed therein and grown in a greenhouse under the conditions of a day length of 15 hours and a temperature of 27° C. (day) and 20° C. (night).

A designed amount of the test compounds formulated in an emulsifiable concentrate or a liquid formulation was diluted with water containing a spreading agent, and the dilution was sprayed over the foliage of the test plant by means of a small hand sprayer at a spray volume of 10 liters per are three times to the same pot, i.e. 14–18 days before, 7–11 days before and 0–4 days before the first heading time of the test plant.

After the heading, flowering and ripening of the test plant, there were harvested 4 heads per pot and spikelets and seeds thereof were counted.

The test was carried out in one pot per a treatment.

The sterility rate was calculated according to the following expression:

Sterility Rate (%)=(1−B/A)×100

A: the number of seeds per spikelet of an untreated plant
B: the number of seeds per spikelet of a treated plant The results are shown in Table 5 by the sterility rates (%). It is shown that the test compounds induced the complete or nearly complete sterility in the test plants.

TABLE 5

| Compound No. | Dosage (g/ha) | Sterility Rate (%) |
|---|---|---|
| 3 | 25 | 100.0 |
| 5 | 2000 | 97.9 |
| 6 | 31.3 | 100.0 |
| 7 | 31.3 | 100.0 |
| 9 | 7.8 | 100.0 |
| 10 | 7.8 | 100.0 |
| 11 | 31.3 | 100.0 |
| 12 | 31.3 | 100.0 |
| 13 | 31.3 | 100.0 |
| 14 | 31.3 | 100.0 |
| 15 | 7.8 | 100.0 |
| 19 | 31.3 | 97.3 |
| 20 | 31.3 | 100.0 |
| 21 | 31.3 | 100.0 |
| 22 | 31.3 | 100.0 |
| 23 | 31.3 | 100.0 |
| 24 | 31.3 | 100.0 |
| 26 | 31.3 | 100.0 |
| 29 | 31.3 | 95.5 |
| 30 | 31.3 | 100.0 |
| 31 | 31.3 | 100.0 |
| 34 | 31.3 | 91.5 |
| 37 | 500 | 100.0 |
| 45 | 250 | 95.1 |
| 47 | 2000 | 100.0 |
| 49 | 250 | 83.2 |

TEST EXAMPLE 2

Male sterility and female fertility test of wheat

1/10000$^a$ Wagnel pots were filled with artificial soil mix and the seeds of wheat (variety: NORIN No. 61), were grown according to the same methods and under the same conditions as in Test Example 1.

The test compound No. 3 was sprayed over the foliage of the test plant once to the same pot according to the method in Test Example 1, 13 days before or 6 days before the first heading time of the test plant.

After the heading and flowering, artificial pollination was carried out as to 2 heads per pot of the pots which appeared to be sterile, using pollens obtained from the heads of untreated plant.

After ripening, there were harvested 4 heads per pot of no artificial pollination and 2 heads per pot of artificial pollination and each of spikelets and seeds thereof was counted.

The test was carried out in one pot per a treatment.

The sterility rate and the fertility rate were calculated according to the following expression:

Sterility rate (%)=(1−B/A)×100

Fertility rate (%)=B/A×100

A: the number of seeds per spikelet of an untreated plant
B: the number of seeds per spikelet of a treated plant The results are shown in Table 6. In table 6, "treated day" shows the number of days before the first heading time of the test plant, in which the test plant was treated with the test compounds, "sterility" is the sterility rate of no artificial pollination heads, and "Fertility" is the fertility rate of artificial pollination.

TABLE 6

| Compound No. | Treated day (Day) | Dosage (g/ha) | Sterility (%) | Fertility (%) |
|---|---|---|---|---|
| 3 | 13 | 50 | 97.5 | 58.0 |
|   | 6  | 50 | 97.5 | 42.5 |

As for the compound No. 3, a sufficient sterilizing effect was shown in the heads by no artificial pollination at both treated days, i.e. 6 days before and 13 days before the first heading time. On the other hand, the fertility rate of the heads by artificial pollination was 58.0% and 42.5% respectively at each treated day and seeds were sufficiently obtained, and thereby the female fertility was recognized.

TEST EXAMPLE 3

Selectivity test as to male sterilizing effect and phytotoxity using wheat

Wheat were grown according to the same method as in Test Example 1. The test compounds, i.e. No. 2 and No. 3, were sprayed over the foliage of the test plant according to the same methods as in Test Example 1 except that the dosage of the test compounds were 2.0, 7.8, 31.3, 125 and 500 g/ha, 10 days before the first heading time of the test plant.

After the heading, flowering and ripening, there were harvested 4 heads per pot and spikelets and seeds thereof were counted.

The sterility rate was calculated according to the same method as in Test Example 1 and rated with an index A, B or C, each of which is equivalent to 80–100%, 50–79% or not more than 50% respectively.

The phytotoxity to heads were observed visually and rated with an index A, B or C, in which "A" indicates the phytotoxity is hardly noticeable, "B" indicates the phytotoxity is acceptable and "C" indicates the phytotoxity is not acceptable.

The test was carried out in three pots per a treatment.

The results were shown in Table 7.

TABLE 7

| Compound No. | | Dosage (g/ha) | | | | |
|---|---|---|---|---|---|---|
| | | 2.0 | 7.8 | 31.3 | 125 | 500 |
| 2 | Sterility | | A | A | | |
| | Phytotoxicity | | A | B | | |
| 3 | Sterility | | | A | A | A |
| | Phytotoxicity | | | A | A | A |
| reference compound* | Sterility | C | A | A | | |
| | Phytotoxicity | A | C | C | | |

*Potassium 1-(4-chlorophenyl)-1,4-dihydro-4-oxo-5-fluorocinnoline-3-carboxylate (the compound disclosed in EP No. 138661).

The compounds No. 2 and No. 3 of the present invention showed a good result for both sterility rate and phytotoxity in a wide range of dosage. On the contrary, with respect to the reference compound, a suitable dosage rate, at which both a sufficient sterility rate and a low phytotoxity can be obtained, was not found. That is, when the phytotoxity was low, the sterility rate was insufficient and when the sterility rate was sufficient, the phytotoxity was high.

TEST EXAMPLE 4

Sterility and female fertility test of rice

Platic pots (volume: 200 ml) were filled with artificial soil mix and seeds of rice were sowed therein and grown under the same conditions as in Test Example 1.

Pots were flooded and then the test compounds were sprayed over the foliage of the test plant according to the same methods as in Test Example 1, 15 days before or 10 days before the first heading time of the test plant.

Two pots were used per one experimental plot. One for an observation of the sterility of the test plant was kept free. The other for the female fertility was artificially pollinated with pollens, which were blown off from other untreated pots placed next thereto, after the heading.

After ripening, there were harvested 4 heads per pot and glumous flower and seeds were counted.

The sterility rate and the fertility rate were calculated according to the following expression:

Sterility rate of heads by no artificial pollination
$(\%) = (1 - B/A) \times 100$ Fertility rate of heads by artificial pollinatio
$(\%) = B/A \times 100$ A: the number of seeds per glumous flower of an untreated plant
B: the number of seeds per glumous flower of a treated plant The results are shown in Table 8. In table 8, the meanings of the terms "treated day", "sterility" and "fertility" are as defined in Test Example 2.

TABLE 8

| Compound No. | Treated day (Day) | Dosage (g/ha) | Sterility (%) | Fertility (%) |
|---|---|---|---|---|
| 2 | 15 | 100 | 100 | 19.1 |
| | 10 | 100 | 94.7 | 15.9 |

As for the compound No. 2, a sufficient sterility rate was shown in the heads by no artificial pollination at both treated days, i.e. 15 days before and 10 days before the first heading time.

On the other hand, seeds were sufficiently obtained from the heads by artificial pollination, and thereby the female fertility was recognized.

TEST EXAMPLE 5

Sterility and female fertility test of morningglory

Plastic pots (volume: 200 ml) were filled with plow-field soil and seeds of morningglory were sowed therein and grown under the same conditions as in Test Example 1 for 7 days. After that, there was carried out a short day treatment (22° C., day length of 8 hours) in a growth chamber for 14 days. After the short day treatment, the test plant was replaced under the same conditions as in Test Example 1.

The test compound No. 30 was sprayed over the foliage of the test plant according to the same methods as in Test Example 1, except that the dosage of the test compound was 125 and 500 g/ha, three times, i.e. 21, 28 and 35 days after sowing to the same pots. The test was carried out i ntwo pots per a treatment.

After flowering, six flowers per a treatment were observed visually and rated with the following index.

Effect to the anther

A: No anther dehiscence
B: Anther dehiscence, few pollen number
C: Anther dehiscence, normal pollen number

Phytotoxicity

A: No or slight phytotoxicity
B: Phytotoxic, but the pistil is normal
C: Phytotoxic to the pistil Artificial pollination was carried out to the flowers of which the effect to the anther was index A and the flowers of untreated control. The anther of the untreated control was hand-emasculated before flowering.

After seed set, the number of seed set flowers was counted and the fertility rate was calculated according to the following expression:

$$\text{Fertility rate (\%)} = \frac{\text{the number of seed set flowers}}{\text{the number of artificial pollinated flowers}} \times 100$$

The results are shown in Table 9.

TABLE 9

| Compound No. | Dosage (g/ha) | Effect to the anther | Phytotoxicity | Fertility rate (%) |
|---|---|---|---|---|
| 30 | 125 | A: 6 flowers | A: 6 flowers | 33 |
| " | 500 | A: 6 flowers | A: 6 flowers | 33 |
| untreated control | 0 | C: 6 flowers | A: 6 flowers | 67 |

The compound No. 30 of the present invention showed good results for sterility, phytotoxicity and fertility rate.

In addition to the ingredients used in the Examples, Formulation Examples and test Examples, other ingredients can be used in the Examples, Formulation Examples and Test Examples as set forth in the specification to obtain substantially the same results.

What we claim is:

1. A composition for inducing male sterility in a plant, which comprises, as an active ingredient, an effective amount of a compound having the formula:

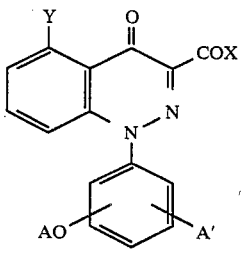

in which X is —OH, —O⁻M⁺, —OR¹ or

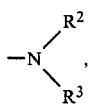

wherein M⁺ is an alkali metal cation, an alkaline earth metal cation or

in which
- $R^4$, $R^5$ and $R^6$ are the same or different and each is hydrogen, $C_1$-$C_6$ alkyl, $C_3$-$C_4$ alkenyl, $C_3$-$C_4$ alkynyl, $C_3$-$C_8$ cycloalkyl, benzyl or phenyl;
- $R^1$ is $C_1$-$C_9$ alkyl, $C_3$-$C_6$ alkenyl, $C_3$-$C_4$ alkynyl, $C_1$-$C_3$ alkoxy ($C_1$-$C_4$) alkyl, $C_3$-$C_8$ cycloalkyl, benzyl or phenyl; and
- $R^2$ and $R^3$ are the same or different and each is hydrogen, $C_1$-$C_6$ alkyl, $C_3$-$C_4$ alkenyl, $C_3$-$C_4$ alkynyl, $C_3$-$C_8$ cycloalkyl, benzyl in which at most two hydrogen atoms at the α-position thereof may be substituted by methyl, $C_2$-$C_3$ hydroxyalkyl or phenyl in which at most three hydrogen atoms thereof may be substituted by the same different $C_1$-$C_2$ alkyl;
- Y is fluorine, chlorine, trifluoromethyl or $C_1$-$C_6$ alkoxy;
- A is $CF_3$, $CHF_2$, $CF_2Cl$, $CF_2BR$, $CF_2CHF_2$, $CH_2CF_3$, $CF_2CHCl_2$, $CFClCHFCl$, $CF_2CHFCl$ or $CF_2CHFCF_3$; and
- A' is hydrogen or halogen;

and an agriculturally acceptable carrier or diluent.

2. The composition of claim 1, in which X is —OH, —O⁻M⁺ or —OR¹.

3. The composition of claim 2, in which A is $CF_3$, $CHF_2$, $CF_2Cl$ or $CF_2Br$.

4. The composition of claim 3, in which Y is fluorine.

5. The composition of claim 3, in which Y is trifluoromethyl.

6. The composition of claim 3, in which Y is $C_1$-$C_4$ alkoxy.

7. A method for inducing male sterility in a plant, which comprises applying an effective amount of a compound having the formula;

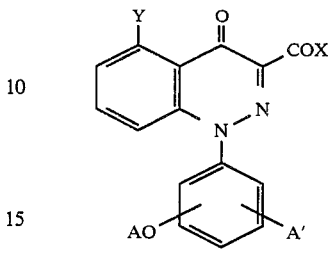

in which X is —OH, —O⁻M⁺, —OR¹ or

wherein M⁺ is an alkali metal cation, an alkaline earth metal cation or

in which
- $R^4$, $R^5$ and $R^6$ are the same or different and each is hydrogen, $C_1$-$C_6$ alkyl, $C_3$-$C_4$ alkenyl, $C_3$-$C_4$ alkynyl, $C_3$-$C_8$ cycloalkyl, benzyl or phenyl;
- $R^1$ is $C_1$-$C_9$ alkyl, $C_3$-$C_6$ alkenyl, $C_3$-$C_4$ alkynyl, $C_1$-$C_3$ alkoxy ($C_1$-$C_4$) alkyl, $C_3$-$C_8$ cycloalkyl, benzyl or phenyl; and
- $R^2$ and $R^3$ are the same or different and each is hydrogen, $C_1$-$C_6$ alkyl, $C_3$-$C_4$ alkenyl, $C_3$-$C_4$ alkynyl, $C_3$-$C_8$ cycloalkyl, benzyl in which at most two hydrogen atoms at the α-position thereof may be substituted by methyl, $C_2$-$C_3$ hydroxyalkyl or phenyl in which at most three of hydrogen atoms thereof may be substituted by the same or different $C_1$-$C_2$ alkyl;
- Y is fluorine, chlorine, trifluoromethyl or $C_1$-$C_6$ alkoxy;
- A is $CF_3$, $CHF_2$, $CF_2Cl$, $CF_2Br$, $CF_2CHF_2$, $CH_2CF_3$, $CF_2CHCl_2$, $CFClCHFCl$, $CF_2CHFCl$ or $CF_2CHFCF_3$; and
- A' is hydrogen or halogen;

and an agriculturally acceptable carrier or diluent to the plant.

* * * * *